United States Patent [19]

Pauly et al.

[11] Patent Number: 4,891,314

[45] Date of Patent: Jan. 2, 1990

[54] AGENT FOR THE DETERMINATION OF PEROXIDASE ACTIVITY, WITH STABILIZER, A PROCESS FOR ITS PREPARATION AND ITS USE

[75] Inventors: Hans E. Pauly, Dautphetal; Herbert Schwarz, Edsdorfergrund, both of Fed. Rep. of Germany

[73] Assignee: Behringwerke Aktiengesellschaft, Marburg an der Lahn, Fed. Rep. of Germany

[21] Appl. No.: 935,332

[22] Filed: Nov. 26, 1986

[30] Foreign Application Priority Data

Nov. 28, 1985 [DE] Fed. Rep. of Germany ........ 3541979

[51] Int. Cl.$^4$ ............................................. C12Q 1/28
[52] U.S. Cl. ....................................... 435/28; 436/66; 436/904
[58] Field of Search .................... 435/28, 188; 436/66, 436/904, 826

[56] References Cited

U.S. PATENT DOCUMENTS

| | | | |
|---|---|---|---|
| 4,063,894 | 12/1977 | Ogawa et al. | 436/66 |
| 4,077,772 | 3/1978 | Geissler et al. | 23/230 |
| 4,340,394 | 7/1982 | Magers et al. | 23/230 |
| 4,503,143 | 3/1985 | Gerber et al. | 435/7 |
| 4,504,579 | 3/1985 | Sun | 435/28 |

FOREIGN PATENT DOCUMENTS 0121317 10/1984 European Pat. Off. .

OTHER PUBLICATIONS

Cook, A. H. et al., "Thiazolidines", in *The Chemistry of Penicillin*, (Ed. Clarke), pp. 921–972, (1949).
"Method of Enzymatic Analysis", H. U. Bergmeyer, Ed., 3rd Ed., vol. 1, pp. 210–221, Verlag Chemie, Weinheim (1983).
Holland et al., Tetrahedron, vol. 30, pp. 3299–3302, (1976).
Garner et al., Cancer Letters, 1, pp. 39–42, (1975).
Garner et al., Journal of Forensic Sciences, 21, pp. 816–821, (1976).
Liem et al., Analytical Biochemistry, 98, pp. 388–393, (1979).
Nakane und Kawaoi, "Journal of Histochemistry and Cytochemistry", vol. 22, No. 12, pp. 1084–1091, (1974).
Voller et al., Bull. of the World Health-Organization, vol. 53, pp. 55–65, (1976).

*Primary Examiner*—Robert J. Warden
*Assistant Examiner*—Toni R. Scheiner
*Attorney, Agent, or Firm*—Finnegan, Henderson, Farabow, Garrett and Dunner

[57] ABSTRACT

An agent for the detection of peroxidase or of pseudoperoxidase activity, and its preparation and its use are described. The agent contains a tetraalkylbenzidine, a penicillin, or its breakdown products obtained by acid hydrolysis, as stabilizer, a peroxide and buffer substances. The agent according to the invention has, as a peroxidase substrate, the advantage over previous tetraalkylbenzidine-containing substrates that it is stable on storage as solution for use, and produces a lower background coloration.

8 Claims, No Drawings

AGENT FOR THE DETERMINATION OF PEROXIDASE ACTIVITY, WITH STABILIZER, A PROCESS FOR ITS PREPARATION AND ITS USE

The present invention relates to an agent for the determination of peroxidase activity by a color reaction, and to a process for its preparation and its use.

An essential prerequisite for the introduction of enzyme immunoassays which are equivalent, in respect of their detection sensitivity, to radioimmunological methods has been the availability of stable marker enzymes and corresponding highly sensitive color-forming reagents with which it was possible to register the catalytic activity of these marker enzymes by use of a straightforward measuring technique. Marker enzymes which have proven particularly suitable for this are the oxidoreductases glucose oxidase and peroxidase. In general peroxidase reactions are among the most frequently used enzymatic detection reactions. For example, all the methods described in "Methods of Enzymatic Analysis", H. U. Bergmeyer, Ed., 3rd Edition, Vol. 1, pages 210–221, Verlag Chemie, Weinheim (1983) are, like the determination of glucose using glucose oxidase, based on the stoichiometric production of hydrogen peroxide. The latter can then be reacted in an oxidation catalyzed by peroxidase, of a colorless substrate to give a colored product which is easily measured quantitatively by spectrophotometry.

Hence, large numbers of chromogenic systems suitable for this reaction catalyzed by peroxidase have been investigated and described (see Bergmeyer). Only few of them meet the requirements for the determination of peroxidase activity in enzyme immunoassays, especially in respect of the detection sensitivity. In general, a chromogenic substrate ought to permit a high rate of conversion and result in a product which has a stable color with a high molar extinction coefficient. Furthermore, substances whose manipulation does not entail any risk to health ought to be preferred. In commercial assay kits for enzyme immunoassays based on peroxidase use is made of, in particular, o-phenylenediamine (OPD) and 2,2'-azinodi-(3-ethylbenzothiazoline-6-sulfonate) (ABTS). Both OPD and ABTS are, as are most peroxidase substrates, mutagenic. One group of substrates which is often used is that of the benzidine type, one of which is tetramethylbenzidine (TMB). TMB is a safe non-mutagenic substitute for carcinogenic peroxidase substrates of the benzidine type, such as benzidine, diaminobenzidine inter alia. A large number of investigations have produced no evidence that this benzidine derivative has mutagenic properties (Tetrahedron 30, 3299 (1976); Cancer Lett. 1, 39 (1975); J. Forensic Sci. 21, 816 (1976)). TMB has been employed since 1974 by various users for the determination of pseudoperoxidase activity of hemoglobin or cytochrome P 450, and it has already been used, by Liem et al., Anal. Biochem. 98, 388–393 (1979), for the detection of peroxidase activity in immune complexes by the immunoperoxidase staining technique. These authors point out, in their conclusions on page 392, that TMB has good staining properties but also that its solubility in the buffer systems usually applied is low and that TMB is subject to oxidative decomposition.

One disadvantage of the chromogenic systems hitherto used and employing TMB for the detection of peroxidase is the low stability of TMB in the mixture which is ready for use. Even in the absence of peroxidase, hydrogen peroxide brings about the development of color, within only a few hours, which makes the substrate solutions useless for an enzyme immunoassay due to the high blank.

Hence there has been a need to find a formulation which contains a tetraalkylbenzidine and is suitable for the determination of peroxidase but does not have the above-mentioned disadvantage. The invention relates to a formulation of this type, to its preparation and to its use.

It has been found, surprisingly, that a tetraalkylbenzidine formulation, which is considerably improved in respect of stability, can be obtained by mixing a solution which contains such a compound, or one of its derivatives, with penicillin, or with penicillin derivatives produced by acid hydrolysis of penicillin, in a concentration between 2.7 $\mu$mol/l and 2.7 mmol/l, preferably between 13.5 $\mu$mol/l and 135 $\mu$mol/l, and adjusting to a pH between 2.5 and 6 by mixing with an aqueous buffer which contains a suitable concentration of hydrogen peroxide. Whereas formulations without an additive of this type show an unacceptable increase in the reagent blank within a time ranging from one to several hours, the addition of penicillin or derivatives thereof increases the stability to a time ranging from one to several weeks.

Hence the invention relates to an agent in the form of a liquid formulation for the detection and for the determination of peroxidase, containing in a predominantly aqueous solution a tetraalkylbenzidine or its salts, penicillin or its breakdown products produced from the bicyclic parent structure of penicillin by weak acid hydrolysis, for example penicillic acid or 6-aminopenicillanic acid, as well as non-cyclic penicillamine, with a content of 2.7 $\mu$mol/l to 2.7 mmol/l, peroxides as substrate for peroxidase, with a content of 0.5 to 50 mmol/l, and buffer substances.

The agent can be prepared by dissolving a solid formulation, for example a lyophilisate, granules or a tablet, where the contents of the components which are used for the liquid formulation—tetraalkylbenzidine, penicillin or its breakdown products, the peroxides and the buffer substances—are in ratios of amounts such that, on dissolution in a defined volume of predominantly aqueous solvent, the components are present in the stated concentrations. The solid formulation can additionally contain additives such as lubricants, fillers and disintegrants, for example polyethylene glycol, urea and bicarbonates.

The tetraalkylbenzidines which can be used are, in particular, those which contain one to three carbon atoms in the alkyl moiety, preferably 3,3',5,5'-tetramethylbenzidine (TMB) or its dihydrochloride. The penicillin which is preferably used is penicillin G or V. Suitable peroxides are sodium perborate, hydrogen peroxide in liquid form or as the solid urea adduct, as well as a system which generates hydrogen peroxide and is composed of D-glucose and glucose oxidase, the concentration being set at 0.5 to 10 mmol/l. Preferred buffer substances are lyotropic substances such as citrates and acetates in concentrations of 5 to 100 mmol/l.

The preparation of a formulation in liquid form entails the tetraalkylbenzidine being dissolved in a first acid solution, of dilute hydrochloric acid or of formic acid, with a pH of 1.5 to 2.0. The penicillin, or its breakdown products produced by acid hydrolysis, are preferably added to this solution.

A second, less acid solution is prepared by dissolving the peroxides, or by introduction thereof when a solution of hydrogen peroxide is used. Examples of substances used for buffering are acetic acid or monosodium or monopotassium citrate whose pH can be adjusted to between 3 and 6 with sodium hydroxide. The said breakdown products of penicillin are added to this second solution if these or a penicillin has not yet been added to the more acid solution.

The formulation ready for use is obtained by mixing the two solutions in a defined ratio.

The invention is illustrated in detail by the Examples which follow, but is not confined to these.

EXAMPLES

1. Preparation of a TMB substrate formulation ready for use

Stock solution 1: TMB dihydrochloride was dissolved, with stirring, at a concentration of 5 g/l, i.e. 16 mmol/l, in double-distilled water, and the pH was adjusted to 1.5 with 5-normal hydrochloric acid. To this solution was added penicillin G, with stirring, in a final concentration of 200 mg/l, i.e. 0.56 mmol/l.

For comparison, stock solution 1 was prepared without addition of penicillin.

Stock solution 2: 1.4 ml of glacial acetic acid, 1.5 ml of 1-normal NaOH and 250 mg, i.e. 3 mmol of $H_2O_2$, of urea-hydrogen peroxide adduct were added to 900 ml of double-distilled water. After dissolution was complete, the volume was made up to 1 l with double-distilled water.

Solution for use: One part by volume of stock solution 1 and 10 parts by volume of stock solution 2 were mixed together.

This solution had an optical density at 650 nm of 0.025. After addition of 5 times the volume of 0.5-normal sulfuric acid, the extinction measured at 450 nm was 0.008.

2. Examination of the stability of the solution for use

The TMB solution for use was prepared as in Example 1 and stored in a refrigerator at 4°–8° C. A solution ready for use was prepared in the same way as in Example 1, but without addition of penicillin G, and was stored. After defined storage times, aliquots of these solutions for use were removed, mixed with 5 times the volume of 0.5-normal sulfuric acid, and the extinction at 450 nm (TMB) was recorded. The results are compiled in the Table below.

TABLE

Stability of the reagent blanks of solutions for use for the determination of peroxidase after 6-fold dilution with 0.5-normal sulfuric acid

| | Reagent blanks after storage at 4° C. for | | | | | |
|---|---|---|---|---|---|---|
| | 0 h | 2 h | 24 h | 48 h | 7 d | 14 d |
| TMB solution | 0.008 | 0.015 | 0.006 | 0.008 | 0.014 | 0.024 |

TABLE-continued

Stability of the reagent blanks of solutions for use for the determination of peroxidase after 6-fold dilution with 0.5-normal sulfuric acid

| | Reagent blanks after storage at 4° C. for | | | | | |
|---|---|---|---|---|---|---|
| | 0 h | 2 h | 24 h | 48 h | 7 d | 14 d |
| for use containing penicillin TMB solution for use without penicillin | 0.010 | 0.038 | 0.105 | 0.365 | — | — |

We claim:

1. An agent for the detection and for the determination of peroxidase activity, comprising a tetraalkylbenzidine or one of its salts, a peroxide or a system generating hydrogen peroxide, one or more buffer substances, and a penicillin or one of its breakdown products produced by acid hydrolysis.

2. An agent as claimed in claim 1, in which the tetraalkylbenzidine contains one to three carbon atoms in the alkyl moiety.

3. An agent as claimed in claim 1, in which the tetraalkylbenzidine is 3,3',5,5'-tetramethylbenzidine.

4. A method of determining the presence of peroxidase activity in a material comprising:
bringing said material into contact with an agent according to claim 1 to form a mixture;
allowing said mixture to stand for a predetermined period of time; and
examining said mixture for the presence of a colored product indicative of the presence of peroxidase.

5. A process for the preparation of an agent for the detection and for the determination of peroxidase activity, which comprises
(a) dissolving a tetraalkylbenzidine to form an acid solution thereof,
(b) adding a penicillin, or a breakdown product obtained by acid hydrolysis of penicillin, to said acid solution,
(c) forming a second solution of peroxide and buffer substances, and
(d) mixing said acid solution with said second solution.

6. The process of claim 5 wherein said acid solution has a pH of from 1.5 to 2.

7. The process of claim 5 wherein said penicillin is added in a concentration of 2.7 μmol/L to 2.7 mmol/L based on the final volume.

8. A process for the preparation of an agent for the detection and for the determination of peroxidase activity, which comprises
(a) dissolving a tetraalkylbenzidine to form an acid solution thereof,
(b) forming a second solution of peroxide and buffer substances,
(c) adding a breakdown product of a penicillin, obtained by acid hydrolysis, to said second solution, and
(d) mixing said acid solution with said second solution.

* * * * *